(12) United States Patent
Ishikawa et al.

(10) Patent No.: US 12,355,297 B2
(45) Date of Patent: Jul. 8, 2025

(54) SURGERY ASSISTANCE DEVICE WITH BACKUP POWER SUPPLY

(71) Applicant: RIVERFIELD INC., Tokyo (JP)

(72) Inventors: Yoshihiro Ishikawa, Tokyo (JP); Satoshi Kano, Tokyo (JP)

(73) Assignee: RIVERFIELD INC., Tokyo (JP)

( * ) Notice: Subject to any disclaimer, the term of this patent is extended or adjusted under 35 U.S.C. 154(b) by 0 days.

(21) Appl. No.: 18/072,239

(22) Filed: Nov. 30, 2022

(65) Prior Publication Data

US 2023/0086127 A1     Mar. 23, 2023

Related U.S. Application Data

(63) Continuation of application No. PCT/JP2020/021603, filed on Jun. 1, 2020.

(51) Int. Cl.
*H02J 9/06*     (2006.01)
*A61B 90/50*     (2016.01)

(52) U.S. Cl.
CPC ............... *H02J 9/06* (2013.01); *A61B 90/50* (2016.02); *A61B 2090/508* (2016.02)

(58) Field of Classification Search
CPC ........................................................ H02J 9/06
See application file for complete search history.

(56) References Cited

U.S. PATENT DOCUMENTS

| | | | | |
|---|---|---|---|---|
| 4,400,626 A | * | 8/1983 | Lacy | H02J 9/061<br>307/66 |
| 4,528,459 A | * | 7/1985 | Wiegel | H02J 9/061<br>307/66 |
| 5,498,913 A | * | 3/1996 | Moritani | H02J 9/061<br>307/64 |
| 5,638,289 A | * | 6/1997 | Yamada | G06F 1/30<br>307/64 |
| 5,892,298 A | * | 4/1999 | Levasseur | E05B 47/00<br>307/64 |
| 6,035,228 A | * | 3/2000 | Yanof | A61B 90/11<br>606/130 |
| 7,170,194 B2 | * | 1/2007 | Korcharz | H02J 9/061<br>307/45 |

(Continued)

FOREIGN PATENT DOCUMENTS

| | | |
|---|---|---|
| JP | 06-063003 A | 3/1994 |
| JP | 08-126990 A | 5/1996 |

(Continued)

OTHER PUBLICATIONS

International Search Report for PCT/JP2020/021603 dated May 8, 2020.
Written Opinion for PCT/JP2020/021603 dated May 8, 2020.

*Primary Examiner* — Adi Amrany
(74) *Attorney, Agent, or Firm* — Sughrue Mion, PLLC

(57) ABSTRACT

A surgery assistance device includes a battery, loads, a manual switch, a power supply, and a backup power supply. The power supply is connected to a mains power supply and to the loads, and outputs a first power supply voltage to the loads. The manual switch is connected to a portion of the loads. The backup power supply is connected to the battery and to the manual switch, and outputs a second power supply voltage to the portion of the loads when the manual switch is closed.

9 Claims, 6 Drawing Sheets

(56) References Cited

U.S. PATENT DOCUMENTS

| | | | |
|---|---|---|---|
| 8,348,931 B2* | 1/2013 | Cooper | A61B 34/37 606/1 |
| 9,240,704 B2* | 1/2016 | Wortberg | H02J 7/1423 |
| 10,907,603 B2* | 2/2021 | Caballero Atienzar | H02J 7/34 |
| 10,916,962 B2* | 2/2021 | Hida | H02J 7/14 |
| 2005/0024905 A1* | 2/2005 | Shiojima | H02J 9/061 363/110 |
| 2005/0099750 A1* | 5/2005 | Takahashi | H02J 9/061 361/92 |
| 2006/0097577 A1* | 5/2006 | Kato | H02J 7/1423 307/10.1 |
| 2009/0225501 A1* | 9/2009 | Luebke | H02J 9/06 307/64 |
| 2010/0265628 A1* | 10/2010 | Blinder | H02J 1/108 307/66 |
| 2013/0249288 A1* | 9/2013 | Haraguchi | H02J 4/00 307/23 |
| 2016/0036371 A1* | 2/2016 | Yamasaki | B62D 5/046 318/400.22 |
| 2016/0359361 A1* | 12/2016 | Tiwari | H02J 9/066 |
| 2018/0014906 A1 | 1/2018 | Fukushima et al. | |
| 2018/0015891 A1* | 1/2018 | Taniguchi | H02J 7/1423 |
| 2018/0360550 A1* | 12/2018 | Nakanishi | A61B 34/70 |
| 2019/0036374 A1* | 1/2019 | Hida | B60L 50/15 |
| 2019/0054870 A1* | 2/2019 | Hida | H02J 7/1423 |
| 2019/0071039 A1* | 3/2019 | Tsukamoto | H02J 7/00304 |
| 2019/0274779 A1 | 9/2019 | Fukushima et al. | |
| 2020/0343763 A1* | 10/2020 | Wataru | B60L 3/0046 |
| 2020/0367979 A1* | 11/2020 | Laakso | A61B 34/37 |
| 2021/0028727 A1* | 1/2021 | Tan | B25J 19/0004 |
| 2021/0154837 A1* | 5/2021 | Kishida | B25J 9/106 |
| 2021/0229610 A1* | 7/2021 | Shimamoto | H02J 7/34 |
| 2021/0315647 A1* | 10/2021 | Tojo | A61B 34/30 |
| 2023/0192017 A1* | 6/2023 | Mitani | H02J 7/345 307/23 |
| 2024/0398490 A1* | 12/2024 | Danziger | A61B 90/06 |

FOREIGN PATENT DOCUMENTS

| | | |
|---|---|---|
| JP | 2003-284726 A | 10/2003 |
| JP | 2014-054695 A | 3/2014 |
| JP | 2015-228922 A | 12/2015 |
| JP | 2016-152906 A | 8/2016 |
| WO | 2018/053349 A1 | 3/2018 |

* cited by examiner

SURGERY ASSISTANCE DEVICE WITH BACKUP POWER SUPPLY

CROSS REFERENCE TO RELATED APPLICATION

This U.S. application is a continuation application of International Application No. PCT/JP2020/021603 filed Jun. 1, 2020, in the Japan Patent Office, the contents of which being incorporated by reference herein in its entirety.

BACKGROUND

The present disclosure relates to a technical field of a surgery assistance device having a function of holding a surgical instrument.

In recent years, surgical operations using a surgery assistance device have become popular. As for the surgery assistance device, a body of a patient and the safety of life need to be considered with first priority. It is hence advantageous to be able to handle a case in which a main power supply cannot be provided, such as a power failure. As such, the operation of the surgery assistance device may be continued at a time of power failure by feeding from a backup battery at the time of the power failure. However, in order to continue the operation of the surgery assistance device, an increase in capacity of the battery is essential, causing a difficulty in downsizing the surgery assistance device.

SUMMARY

It is an aspect to provide a surgery assistance device that can realize downsizing of a backup battery while offering appropriate responses even at a time of a power failure or the like.

According to an aspect of one or more embodiments, there is provided a surgery assistance device comprising a power supply configured to output a power supply voltage by using an external power supply; a backup power supply configured to output a power supply voltage by using a battery; a first power supply voltage path configured to supply the power supply voltage of the power supply to a plurality of loads; a manual switch; and a second power supply voltage path configured to be capable of supplying the power supply voltage of the backup power supply to some of the loads among the plurality of loads when the manual switch is operated.

According to another aspect of one or more embodiments, there is provided a surgery assistance device comprising a battery; a plurality of loads; a manual switch; a power supply connected to an external power supply and configured to output a first power supply voltage based on power supplied from the external power supply; a backup power supply connected to the battery and configured to output a second power supply voltage based on power supplied from the battery; a first power supply voltage path configured to supply the first power supply voltage to the plurality of loads; and a second power supply voltage path configured supply the second power supply voltage to a portion of the plurality of loads based on an operation of the manual switch.

According to yet another aspect of one or more embodiments, there is provided a surgery assistance device comprising a battery; a plurality of loads; a manual switch connected to a portion of the plurality of loads; a power supply connected to a mains power supply and to the plurality of loads, the power supply being configured to output a first power supply voltage to the plurality of loads; a backup power supply connected to the battery and to the manual switch, wherein the backup power supply is configured to output a second power supply voltage to the portion of the plurality of loads when the manual switch is closed.

BRIEF DESCRIPTION OF DRAWINGS

The above and/or other aspects will become apparent and more readily appreciated from the following description of exemplary embodiments, taken in conjunction with the accompanying drawings in which.

DETAILED DESCRIPTION

Figure 1:
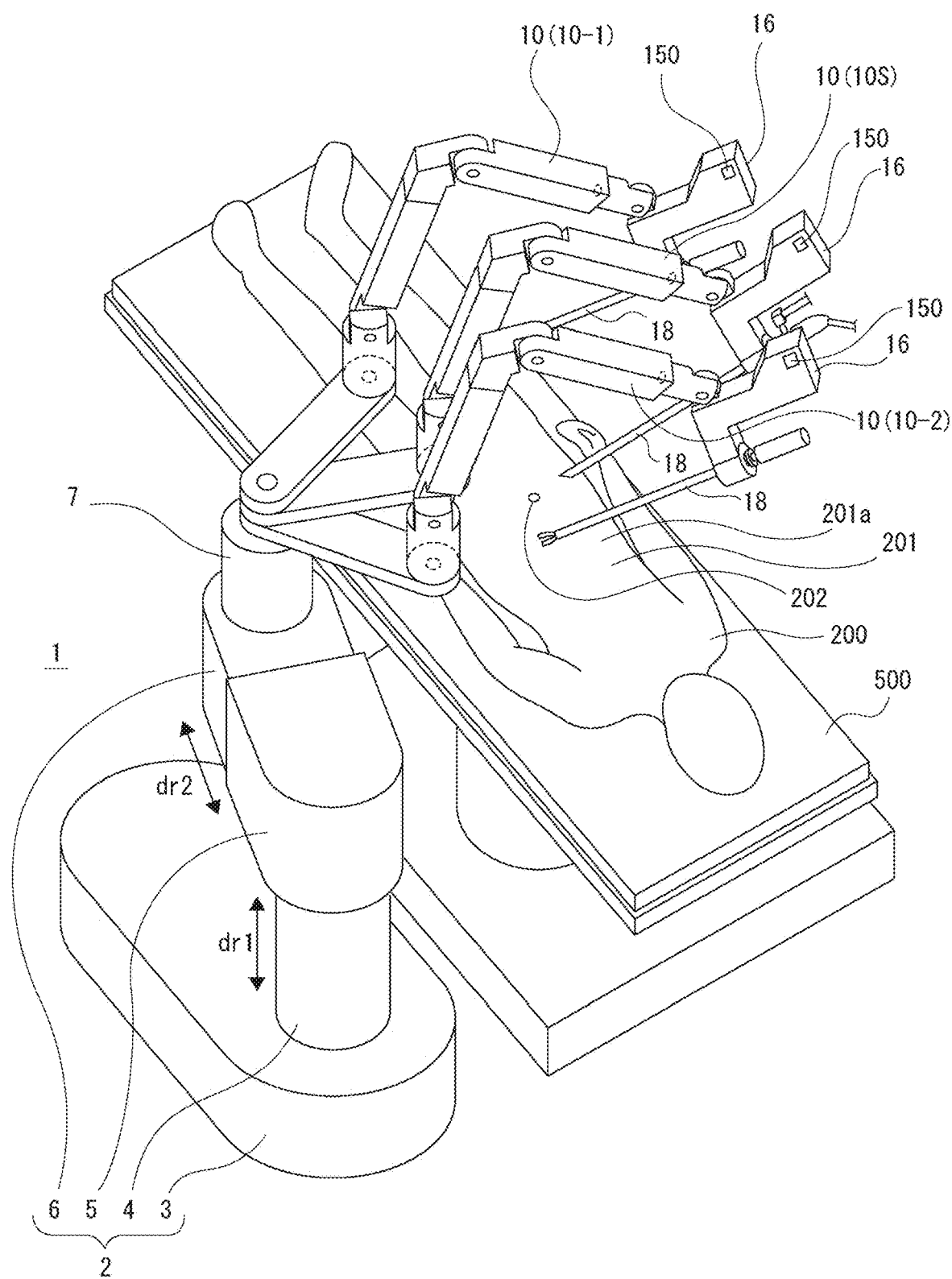
FIG. 1 is a diagram of assistance in explaining a surgery assistance device according to some embodiments.

As explained above, in recent years, surgical operations using a surgery assistance device have become popular. Such a surgery assistance device holds a surgical instrument such as an endoscope or forceps, and includes a plurality of movable bodies for changing the position and pose of the surgical instrument.

There are many surgical instruments provided with an electrically operated actuator/motor, and the surgical instruments are provided with sensors, encoders, and electromagnetic brakes accompanying these actuators/motors as well as driving circuits, control circuits, detecting circuits, and the like corresponding to these devices.

A power supply including a power supply circuit is provided to supply a power supply voltage to these devices and circuits. The power supply generates a predetermined direct-current power supply voltage by using an external power supply (typically a commercial/mains alternating-current power supply), and supplies the direct-current power supply voltage to the circuits/devices.

As discussed above, a body of a patient and the safety of life need to be considered with first priority. It is hence advantageous to be able to handle a case in which a main power supply cannot be provided, such as during a power failure. As such, the operation of the surgery assistance device may be continued at a time of power failure by feeding power from a backup battery at the time of the power failure.

However, in order to continue the operation of the surgery assistance device, an increase in capacity of the battery is essential, causing a difficulty in downsizing the surgery assistance device.

Accordingly, exemplary embodiments are directed to a surgery assistance device that can realize downsizing of a backup battery while offering appropriate responses even at a time of a power failure or the like.

A surgery assistance device according to some embodiments includes a power supply configured to output a predetermined power supply voltage by using an external power supply, a backup power supply configured to output a predetermined power supply voltage by using a battery, a first power supply voltage path configured to supply the power supply voltage of the power supply to a plurality of loads, a manual switch, and a second power supply voltage path configured to be capable of supplying the power supply voltage of the backup power supply to some of the loads among the plurality of loads when the manual switch is operated.

The term "load" as used in this specification denotes a circuit or a device to which the power supply voltage is supplied. The power supply supplies the power supply voltage to the plurality of loads, and the backup power supply supplies the power supply voltage to only some of the loads.

In the surgery assistance device according to some embodiments described above, one or a plurality of electromagnetic brakes may be included as the load(s) to be supplied with the power supply voltage of the backup power supply via the second power supply voltage path.

That is, the backup power supply voltage is supplied to the electromagnetic brake(s) in one or a plurality of movable sections provided to the surgery assistance device.

The electromagnetic brake(s) in this case is (are) a non-excitation actuated brake that applies braking and maintains the state when energization thereof is turned off.

In the surgery assistance device according to some embodiments described above, the load(s) to be supplied with the power supply voltage of the backup power supply via the second power supply voltage path by operation of the manual switch may be only one or a plurality of electromagnetic brakes.

That is, only the electromagnetic brake(s) is (are) supplied with the backup power supply voltage according to operation of the manual switch.

In the surgery assistance device according to some embodiments described above, a plurality of surgical instruments may be held by a plurality of arms, and the manual switch and the second power supply voltage path that conducts according to operation of the manual switch may be provided for each arm.

A configuration is adopted in which the backup power supply voltage can be supplied to each arm by operation of the manual switch.

In the surgery assistance device according to some embodiments described above, the first power supply voltage path and the second power supply voltage path may each be connected to a common path on cathode electrode sides of diodes, and some of the loads may be supplied with the power supply voltage by the common path.

The first power supply voltage path and the second power supply voltage path are each connected to anodes of the diodes, and the cathode electrode sides of the diodes are connected to wiring of the common path to the load(s).

According to some embodiments, even when the power supply cannot supply the power supply voltage at a time of a power failure or the like, the backup power supply can supply the power supply voltage to some of the loads. In this case, limiting destinations to which the power supply voltage is supplied to some of the loads makes it possible to realize operation necessary at least at a time of an emergency such as a power failure and reduce power consumption. It is thus possible to facilitate downsizing of the battery.

A surgery assistance device according to an embodiment will hereinafter be described in the following order.

<1. General Configuration of Surgery Assistance Device and Like>
<2. Configuration of Auxiliary Power Supply>
<3. Specific Example of Power Supply System>
<4. Effects and Modifications of Embodiments>

1. General Configuration of Surgery Assistance Device and Like

According to some embodiments, a surgery assistance device of a type used in a state of being installed on the floor of an operating room or the like will be taken as an example. However, the scope of application of the surgery assistance device according to some embodiments is not limited to the type used in a state of being installed on the floor of an operating room or the like, and the surgery assistance device according to some embodiments can also be applied to various kinds of surgery assistance devices such as a type used in a state of being attached to the ceiling or wall surface of an operating room and the like.

FIG. 1 depicts an example of a surgery assistance device 1.

An operating table 500 is installed in the operating room. A patient 200 is laid down on his or her back, for example, on the operating table 500. A port 202 is formed in a part forming a body cavity 201 of the patient 200, for example, an abdominal wall 201a. A part (distal end portion) of a surgical instrument to be described later is inserted into the port 202 when a surgical operation is performed. The port 202 is a small hole into which a shaft-shaped surgical instrument is inserted.

The surgery assistance device 1 mainly includes a base 2, a stage 7 attached onto the base 2, one or a plurality of arms 10 attached to the stage 7, a surgical instrument holding device(s) 16 attached to a distal end(s) of the arm(s) 10, and a surgical instrument(s) 18 held by the surgical instrument holding device(s) 16 in a replaceable manner.

A base portion 3 mounted on the floor of the operating room or the like is formed in the base 2. A raising and lowering mechanism 4 is attached to the base portion 3. A base arm rear 5 is raised and lowered in an upward-downward direction (dr1) by the raising and lowering mechanism 4, and is adjustable to an appropriate height position.

A base arm front 6 is attached to the base arm rear 5 by a device that can be extended in a horizontal direction (dr2), so that the position of the stage 7 attached to a distal end of the base arm front 6 can be adjusted.

The stage 7 is formed on the base arm front 6, and pivotally supports the arm(s) 10.

In the example of FIG. 1, three units of a first arm 10-1, a second arm 10-2, and a scope arm 10S are attached as arms 10, and are each rotatable on the stage 7.

Each arm 10 includes one or a plurality of joint sections and rotary sections, and is formed with a device that easily moves a distal end of the arm to any position.

A surgical instrument holding device 16 is attached to a distal end portion of the arm 10 via a gimbal device or the like. Each of the arms 10-1 and 10-2 holds a surgical instrument 18 such as forceps by the surgical instrument holding device 16.

In addition, the surgical instrument holding device 16 of the scope arm 10S holds a scope as the surgical instrument 18.

The scope is, for example, provided as a scope device including an endoscope. The scope includes, for example, a shaft extending in a forward-rearward direction, a camera head coupled to a rear end portion of the shaft, a light guide coupled to an intermediate portion of the shaft, and the like.

A distal end portion of the shaft of the surgical instrument 18 such as the scope or forceps is inserted into the body cavity 201 from the port 202 formed in the patient 200.

In a state in which the distal end portion of the shaft is inserted into the body cavity 201, illuminating light is applied from the distal end portion of the shaft of the scope, and an imaging element photographs the state of the inside of the body cavity 201. The state of the inside of the body cavity 201 that is photographed by the imaging element is sent out as a photographed image signal to an unillustrated operating device which is operated by an operator (surgeon). Thus, the operator can remotely observe the state of the inside of the body cavity 201.

In addition, the operator can perform surgery by remotely operating the forceps attached to the arms 10-1 and 10-2.

All or some of movable sections as the joint sections and the rotary sections in each arm 10 are driven by a built-in motor or actuator according to remote operation from the operating device.

While the surgery assistance device 1 that can operate the three surgical instruments 18 by the three arms 10 has been illustrated, it suffices for the surgery assistance device 1 to be able to handle one or more surgical instruments by at least one or more arms.

Such a surgery assistance device 1 makes it possible to perform a surgical operation by remotely controlling the one or plurality of surgical instruments and thus shorten the surgery time, and also makes it possible to perform an advanced surgical operation by using a plurality of surgical instruments of different kinds.

All or some of the movable sections as the joint sections and the rotary sections in each arm 10 are driven by a built-in motor or actuator, and are braked by an electromagnetic brake.

An electromagnetic brake used is, for example, a non-excitation actuated brake that applies braking and maintains the state when energization thereof is turned off.

In a state in which the electromagnetic brake is energized, the joint section or the rotary section can be moved by the hands of a medical staff. For example, the medical staff manually holds and moves the arm 10 itself, the part of the surgical instrument holding device 16 at a distal end of the arm 10, or the like, so that movement of the arm 10, movement of the surgical instrument 18, or the like can be performed.

Figure 2:
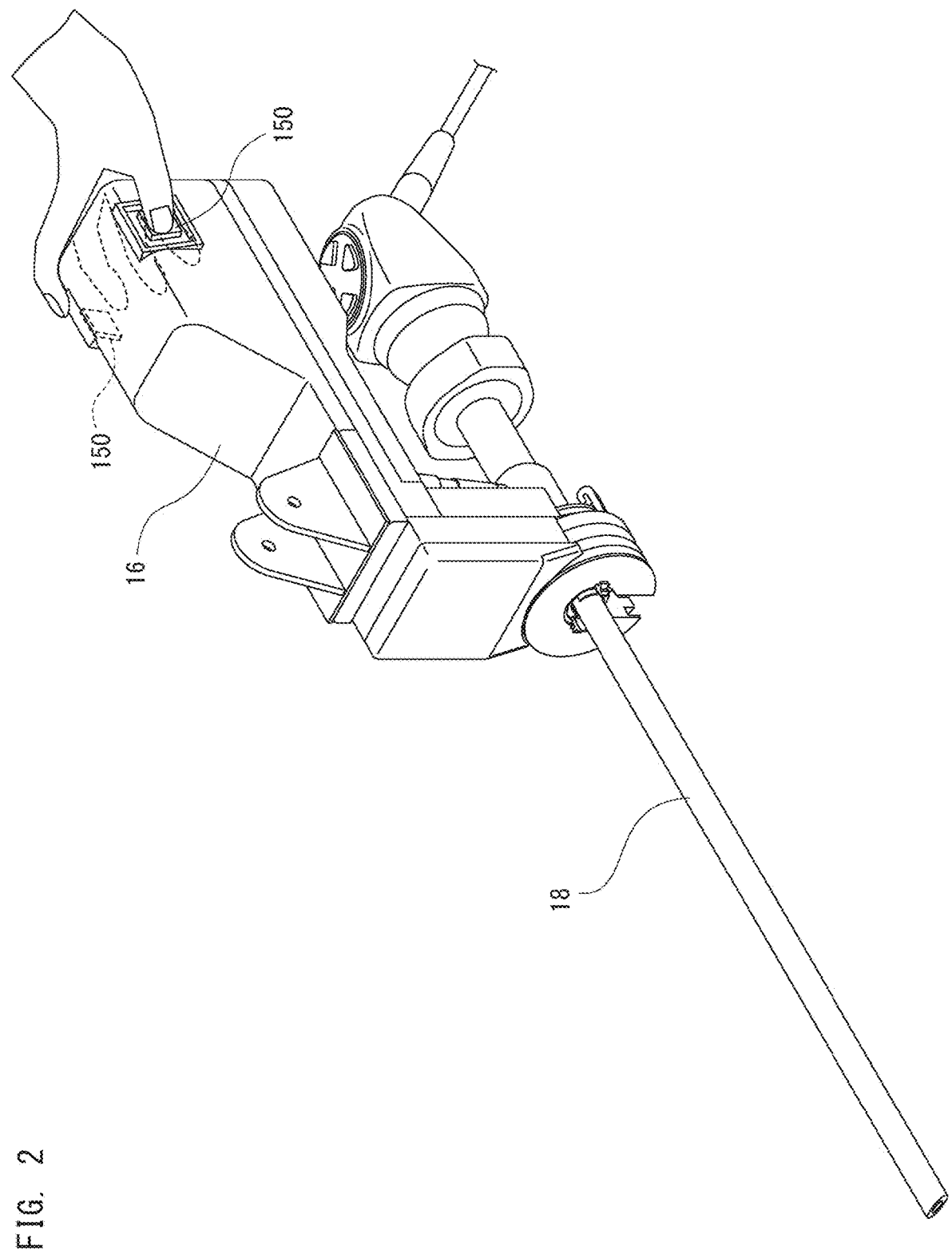
FIG. 2 is a diagram of assistance in explaining manual switches in the surgery assistance device according to some embodiments.

Each surgical instrument holding device 16 is provided with manual switches 150. FIG. 2 depicts the surgical instrument holding device 16 on an enlarged scale. The manual switches 150 are, for example, provided to left and right upper portions of a casing of the surgical instrument holding device 16.

This configuration, for example, makes it easy for the medical staff to grip the surgical instrument holding device 16 while pushing the manual switch 150.

The manual switches 150 are switches for energizing some of loads (circuits/devices) such as the above-described electromagnetic brake. Even at an off time of a main power supply and at a time of a power failure, pressing the manual switch 150 energizes the electromagnetic brake and releases braking. Hence, the position of the surgical instrument 18 or the like can be moved by the medical staff gripping and moving the surgical instrument holding device 16 as in FIG. 2.

The manual switches 150 are of a momentary type that is on only while being pressed.

FIG. 2 depicts an example in which two manual switches 150 are provided to one surgical instrument holding device 16. The two manual switches 150 are both switches for energization of the electromagnetic brake. Either of the two manual switches 150 that is easier to press can be pressed when the surgical instrument holding device 16 is gripped, for example. Thus, a switch operation is performed easily when necessary, irrespective of the orientation and pose of the surgical instrument holding device 16.

It suffices to provide at least one manual switch 150 to the surgical instrument holding device 16. However, a larger number of manual switches 150 may be provided.

While the manual switches 150 are provided to the surgical instrument holding device 16 of each arm 10 as in FIG. 1, there is also a possible example in which one manual switch 150 is provided to the whole of the surgery assistance device 1. The manual switches 150 are not limited to being provided on the surgical instrument holding device 16.

2. Configuration of Auxiliary Power Supply

Figure 3:
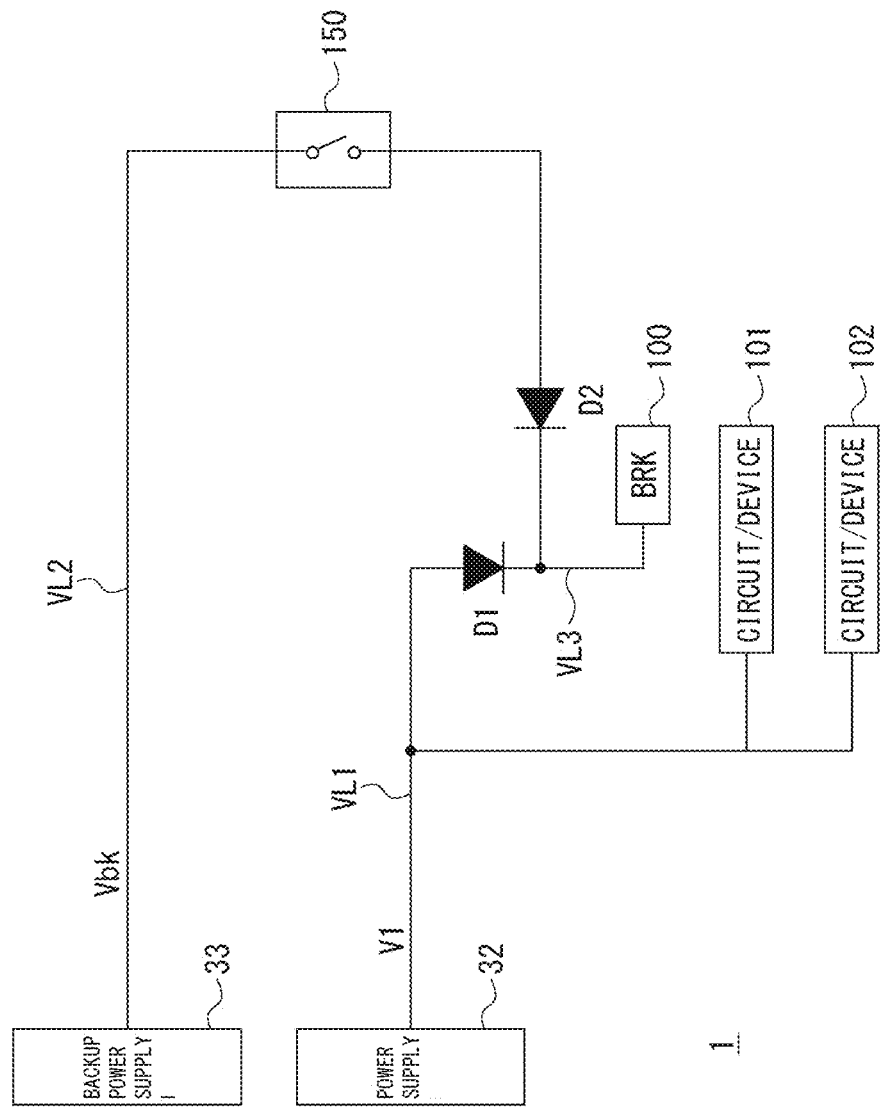
FIG. 3 is a diagram of assistance in explaining power supply voltage paths of the surgery assistance device according to some embodiments.

A power supply system in such a surgery assistance device 1 will be described. FIG. 3 depicts a configuration of principal parts of the power supply system.

As illustrated in FIG. 3, the surgery assistance device 1 according to some embodiments includes a power supply 32 that outputs a power supply voltage V1 by using an external power supply, that is, an alternating-current power supply, and a backup power supply 33 that outputs a backup power supply voltage Vbk by using a backup battery. In some embodiments, the alternating-current power supply may be a mains supply.

A first power supply voltage path VL1 which supplies the power supply voltage V1 of the power supply 32 to a plurality of loads, that is, an electromagnetic brake 100, circuits/devices 101 and 102, and the like in FIG. 3, is formed.

A second power supply voltage path VL2 which can supply the backup power supply voltage Vbk to some of the loads (e.g., the electromagnetic brake 100) among the plurality of loads when the manual switch 150 described above is operated is provided.

In the case of this configuration, during a normal time during which the main power supply is on, the power supply voltage path VL1 feeds each load from the power supply 32, and each load (e.g., the electromagnetic brake 100, the circuits/devices 101 and 102, and the like in FIG. 3) thereby operates. The load is a general term of parts that need to be energized for operation, such as the electromagnetic brake 100, devices such as motors, encoders, or sensors, and circuits such as motor drivers for driving these devices.

Here, supposing that the power supply 32 is configured to receive alternating-current power and generate the power supply voltage V1 by an AC (Alternating Current)/DC (Direct Current) converter, the power supply 32 cannot feed each load at a time of a power failure. For example, the alternating-current power may be supplied from a mains supply.

The backup power supply 33 employing a battery backup configuration is provided. When the manual switch 150 is pressed, the power supply voltage path VL2 supplies the backup power supply voltage Vbk to the load.

However, the power supply voltage path VL2 is configured to feed some of the loads, or only the electromagnetic brake 100, in the present example. That is, in some embodiments, the backup power supply 33 makes only some of the loads operable rather than enabling all of the loads to operate.

In the case of the embodiment illustrated in FIG. 3, both of the power supply voltage paths VL1 and VL2 are connected to the electromagnetic brake 100, and there is adopted a configuration in which the cathode sides of diodes D1 and D2 connected to the power supply voltage paths VL1 and VL2 are connected to a common path VL3. Thus, feeding through the power supply voltage path VL1 or the power supply voltage path VL2 is made possible by use of a common power supply voltage input terminal of the device as the electromagnetic brake 100.

3. Specific Example of Power Supply System

Figure 5:
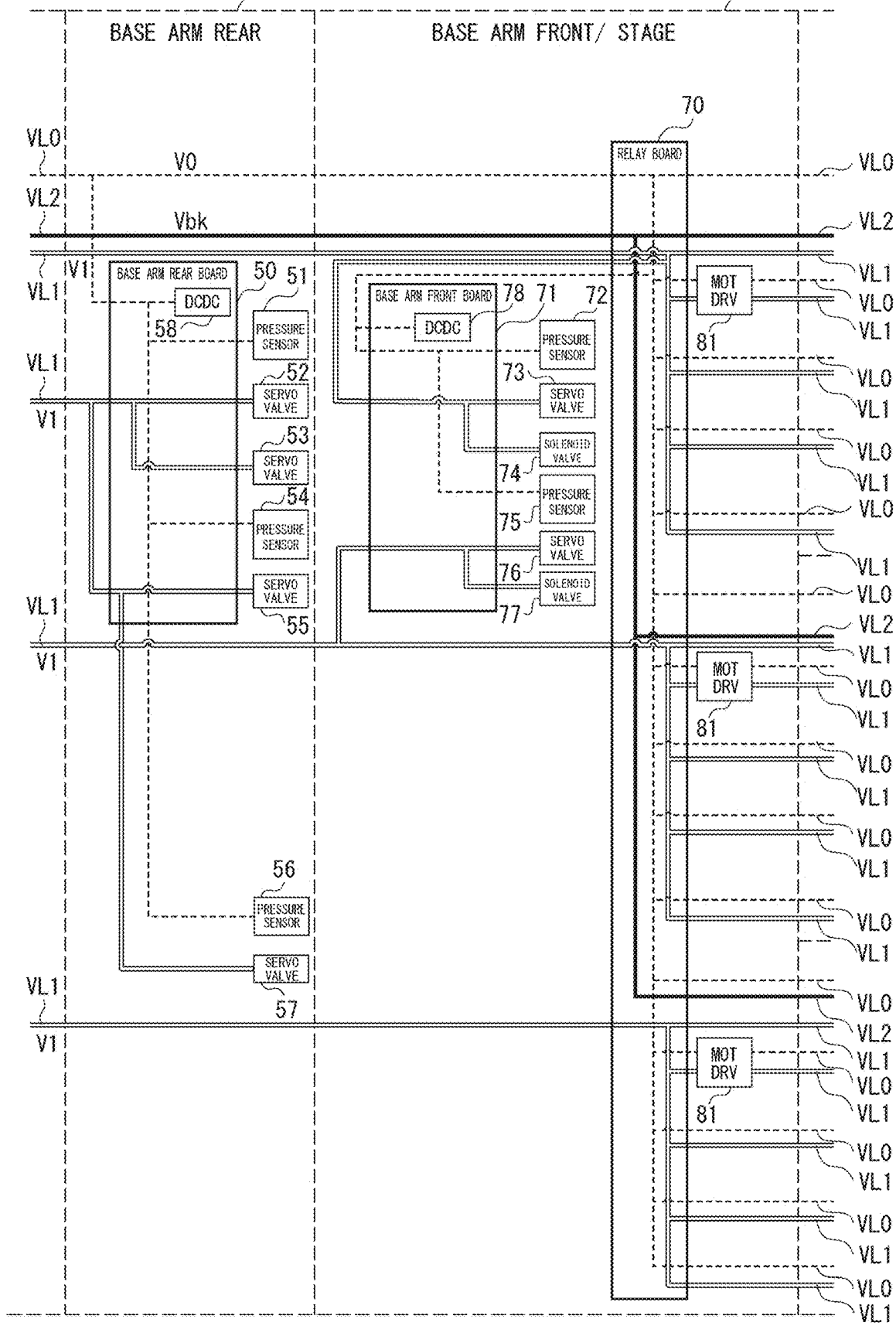
FIG. 5 is a diagram of assistance in explaining the power supply system of the surgery assistance device according to some embodiments.
Figure 6:
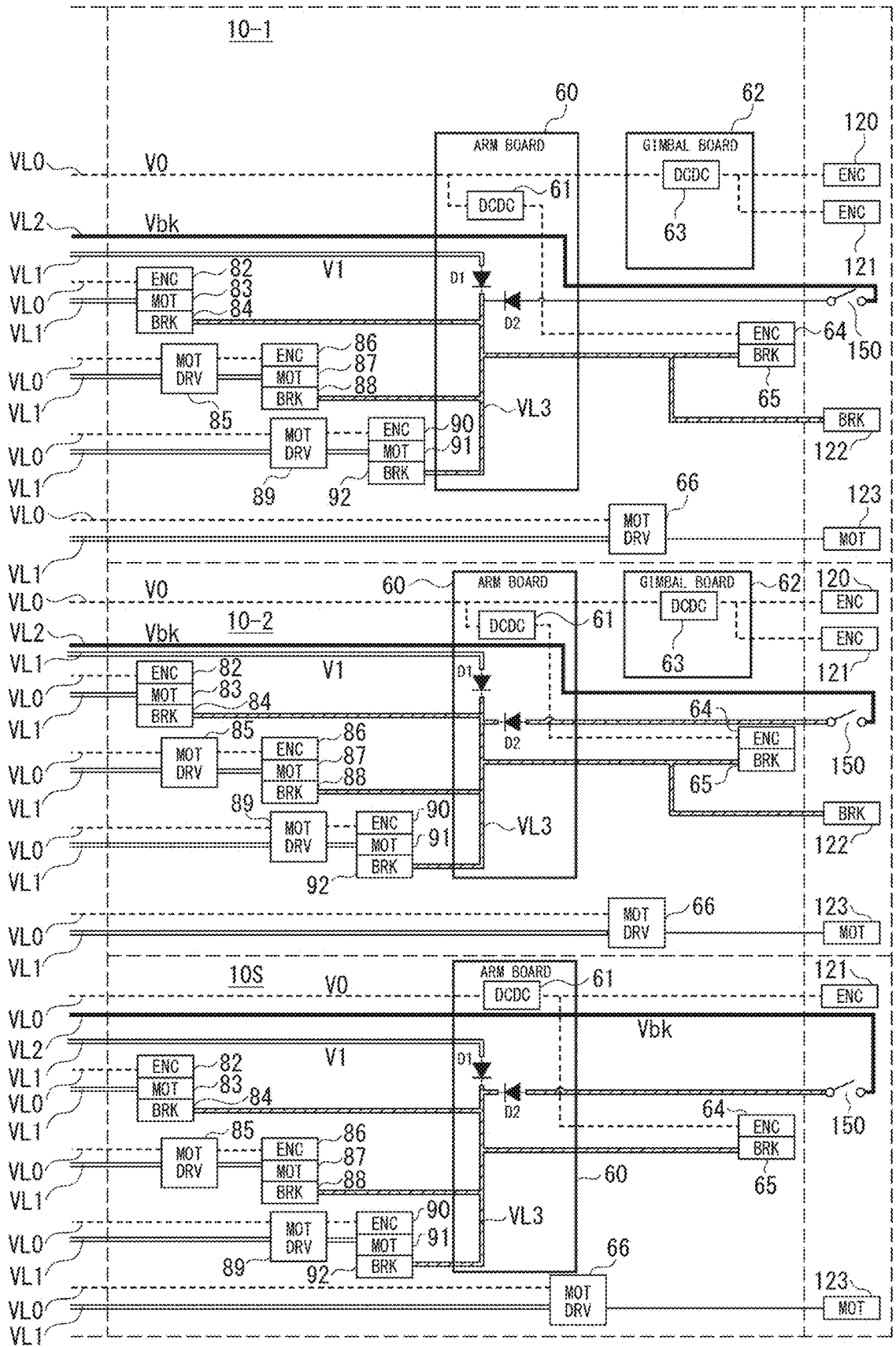
FIG. 6 is a diagram of assistance in explaining the power supply system of the surgery assistance device according to some embodiments.

A specific example of the power supply system of the surgery assistance device 1 having the configuration of FIG. 3 described above is illustrated in FIG. 4, FIG. 5, and FIG. 6. These figures illustrate, as three separate diagrams, the power supply system from the base 2 to the movable sections at the distal ends of the arms 10. That is, FIG. 5 is a continuation of FIG. 4, and FIG. 6 is a continuation of FIG. 5.

In order to avoid complicated description, the power supply system actually provided to the surgery assistance device 1 is not illustrated in its entirety. Many parts not directly related to the subject matter of some embodiments are not illustrated, the parts being filters provided at respective positions, elements for stabilization or the like, and the like.

Figure 4:
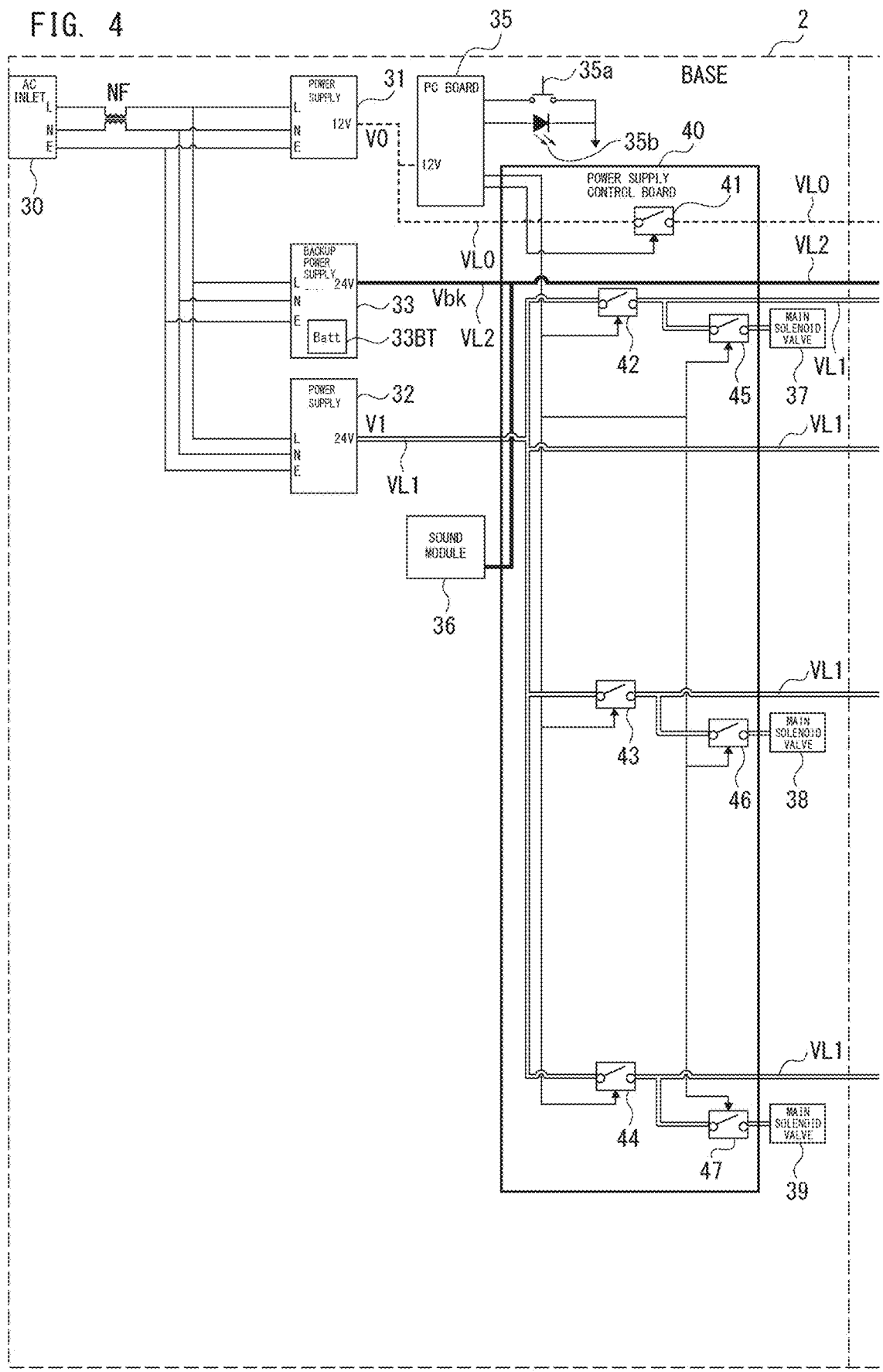
FIG. 4 is a diagram of assistance in explaining a power supply system of the surgery assistance device according to some embodiments.

FIG. 4 illustrates a configuration provided to the base 2 (for example, inside the base portion 3).

Power supplies 31 and 32 and a backup power supply 33 are provided as power supply circuits. These power supply circuits have an L (live) terminal, an N (neutral) terminal, and an E (earth) terminal connected to an AC inlet 30, and are supplied with an alternating-current voltage via a noise filter NF.

The power supply 31 receives the alternating-current voltage, generates a direct-current power supply voltage V0 of 12 V by an AC/DC converter, and outputs the direct-current power supply voltage V0 to a power supply voltage path VL0.

The power supply 32 receives the alternating-current voltage, generates a direct-current power supply voltage V1 of 24 V by an AC/DC converter, and outputs the direct-current power supply voltage V1 to the power supply voltage path VL1.

The backup power supply 33 includes a backup battery 33BT. The backup power supply 33 obtains a direct-current output voltage of 24 V which results from stabilization of a battery voltage of the backup battery 33BT or a direct-current output voltage of 24 V which results from voltage conversion from the battery voltage by a DC/DC converter. This is set as the backup power supply voltage Vbk, and the backup power supply voltage Vbk is output to the power supply voltage path VL2.

The backup power supply 33 also includes a charging circuit configuration that is supplied with alternating-current power from the AC inlet and that charges the backup battery 33BT.

The backup power supply 33 may include an AC/DC converter in addition to the above-described charging circuit configuration, and at a normal time (at a time of no power failure or the like), the backup power supply 33 may obtain a direct-current of 24 V by the AC/DC converter, and output this direct-current of 24 V as the backup power supply voltage Vbk to the power supply voltage path VL2.

In FIGS. 4-6, for distinction, the power supply voltage path VL1 is represented by a double line, the power supply voltage path VL2 is represented by a thick line, and the power supply voltage path VL0 is represented by a broken line.

The common path VL3 appearing in FIG. 6 is represented as a hatched double line.

A PC board 35 is a board mounted with a microcomputer as a control circuit. The PC board 35 is supplied with the power supply voltage V0 from the power supply 31 as an operating power supply voltage.

The PC board 35 is configured to monitor the operation of a main power supply switch 35a. The PC board 35 performs on/off control of the main power supply according to operation of the main power supply switch 35a by the operator. In addition, when the main power supply is turned on, the on state of the main power supply is presented by light emission of an LED (Light Emitting Diode) as a light emitting unit 35b.

For the on/off control of the power supply according to the operation of the main power supply switch 35a, control signals are output from the PC board 35 to switches 41, 42, 43, 44, 45, 46, and 47 that are provided to a power supply control board 40 and formed by a FET (Field Effect Transistor), for example.

The switch 41 is a switch that turns on/off the supply of the power supply voltage V0 of 12 V by the power supply voltage path VL0.

The power supply voltage V0 of 12 V is used mainly as operating power for sensors of respective parts and operating power for circuits such as encoders and DC/DC converters.

The switches 42, 43, 44, 45, 46, and 47 are switches that turn on/off the supply of the power supply voltage V1 of 24 V by the power supply voltage path VL1.

The power supply voltage V1 of 24 V is used mainly as operating power for actuators such as motors, electromagnetic brakes, and solenoid valves of respective parts, and the like.

The power supply voltage path VL1 from the power supply 32 is branched on the power supply control board 40 into three paths corresponding to the three arms 10. The switches 42, 43, and 44 are arranged on the respective paths.

The power supply voltage path VL1 is further branched in respective stages subsequent to the switches 42, 43, and 44. The switches 45, 46, and 47 are arranged on branched paths on one side. The switches 45, 46, and 47 turn on/off the supply of the power supply voltage V1 to main solenoid valves 37, 38, and 39 provided inside the base 2.

The control signals from the PC board 35 can individually control each of the switches 41, 42, 43, 44, 45, 46, and 47, or can control the switches 41, 42, 43, 44, 45, 46, and 47 simultaneously.

For example, because the switches 42, 43, and 44 are individually provided to the power supply voltage paths VL1 of the respective arms 10, power can be turned on in arm 10 units.

A sound module 36 that, for example, outputs guide sound or the like is provided inside the base 2. The sound module 36 is supplied with the backup power supply voltage Vbk by the power supply voltage path VL2. This configuration is to enable sound guidance or the like even at a time of a power failure.

FIG. 5, continuously from FIG. 4, illustrates a power supply system formed inside the base arm rear 5, the base arm front 6, and the stage 7.

A base arm rear board 50 is disposed in the base arm rear 5.

The power supply voltage path VL0 is formed via the base arm rear board 50, and the power supply voltage V0 is supplied to a DC/DC converter 58. The DC/DC converter 58 receives the power supply voltage V0, generates a necessary voltage, and supplies the voltage to an unillustrated circuit on the board.

The power supply voltage V0 is supplied to pressure sensors 51, 54, and 56 via the base arm rear board 50.

Servo valves 52, 53, 55, and 57 provided to the base arm rear 5 are supplied with the power supply voltage V1 by the power supply voltage path VL1.

A relay board 70 is provided for relay of the power supply system between the base arm front 6 and the stage 7 and each arm 10.

A base arm front board 71 is disposed in the base arm front 6.

The power supply voltage path VL0 is formed via the relay board 70 and the base arm front board 71, and the power supply voltage V0 is supplied to a DC/DC converter 78 mounted on the base arm front board 71. The DC/DC converter 78 receives the power supply voltage V0, generates a necessary voltage, and supplies the voltage to an unillustrated circuit on the board.

The power supply voltage V0 is supplied to pressure sensors 72 and 75 via the base arm front board 71.

Servo valves 73 and 76 and solenoid valves 74 and 77 provided to the base arm front 6 or the stage 7 are supplied with the power supply voltage V1 by the power supply voltage path VL1.

The stage 7 is provided with three motor drivers 81 in correspondence with the respective arms 10.

Each of the motor drivers 81 is supplied with the power supply voltages V0 and V1 as power for circuit operation, power for encoder operation, and power for motor operation.

As illustrated in FIG. 6, via each of the motor drivers 81, an encoder 82 in each arm 10 (10-1, 10-2, or 10S) is supplied with the power supply voltage V0, and a motor 83 in each arm 10 is supplied with a driving voltage based on the power supply voltage V1. An electromagnetic brake 84 is separately supplied with the power supply voltage V1 or the backup power supply voltage Vbk via the common path VL3.

The motor driver 81, the encoder 82, the motor 83, and the electromagnetic brake 84 constitute a driving system that performs rotation operation of the arm 10 on the stage 7.

The encoder 82 (and encoders 86, 90, 120, and 121 to be described later) is, for example, a device that detects a rotational position state, the device being a rotary encoder or the like.

As illustrated in FIG. 6, each arm 10 is respectively provided with a motor driver 85.

The motor driver 85 is supplied via the relay board 70 (see FIG. 5) with the power supply voltages V0 and V1 as power for circuit operation, power for encoder operation, and power for motor operation.

Inside each arm 10, via the motor driver 85, an encoder 86 is supplied with the power supply voltage V0, and a motor 87 is supplied with a driving voltage based on the power supply voltage V1. An electromagnetic brake 88 is separately supplied with the power supply voltage V1 or the backup power supply voltage Vbk via the common path VL3.

The motor driver 85, the encoder 86, the motor 87, and the electromagnetic brake 88 constitute a driving system for one of joints of the arm 10.

Each arm 10 is respectively provided with a motor driver 89.

The motor driver 89 is supplied via the relay board 70 (see FIG. 5) with the power supply voltages V0 and V1 as power for circuit operation, power for encoder operation, and power for motor operation.

Inside each arm 10, via the motor driver 89, an encoder 90 is supplied with the power supply voltage V0, and a motor 91 is supplied with a driving voltage based on the power supply voltage V1. An electromagnetic brake 92 is separately supplied with the power supply voltage V1 or the backup power supply voltage Vbk via the common path VL3.

The motor driver 89, the encoder 90, the motor 91, and the electromagnetic brake 92 also constitute a driving system for one of the joints of the arm 10.

Each arm 10 is respectively provided with a motor driver 66.

The motor driver 66 is supplied via the relay board 70 (see FIG. 5) with the power supply voltages V0 and V1 as power for circuit operation and power for motor operation.

In each arm 10, a motor 123 is supplied with a driving voltage based on the power supply voltage V1 via the motor driver 66.

In each arm 10, an arm board 60 is respectively mounted to relay the power supply voltage paths VL0, VL1, and VL2.

The arm board 60 generates a required voltage from the power supply voltage V0 by a DC/DC converter 61, and supplies the voltage to an encoder 64.

The common path VL3 is formed in each arm board 60, and the common path VL3 connects the power supply voltage paths VL1 and VL2. The power supply voltage path VL1 is connected to an anode of a diode D1 on the arm board 60. The power supply voltage path VL2 is relayed by the arm board 60, is thereafter returned to the arm board 60 via the manual switch 150, and is then connected to an anode of a diode D2.

Cathodes of the diodes D1 and D2 are connected to the common path VL3. The common path VL3 is a line that supplies a power supply voltage to the above-described electromagnetic brakes 84, 88, and 92.

In each arm 10, an electromagnetic brake 65 is also supplied with the power supply voltage V1 or the backup power supply voltage Vbk by the common path VL3.

In the arms 10-1 and 10-2, an electromagnetic brake 122 is also supplied with the power supply voltage V1 or the backup power supply voltage Vbk by the common path VL3.

During an on time of the main power supply, the electromagnetic brakes 84, 88, 92, 65, and 122 are supplied with the power supply voltage V1 via the power supply voltage path VL1, the diode D1, and the common path VL3.

During a power failure or during an off time of the main power supply, when the manual switch 150 is turned on, the electromagnetic brakes 84, 88, 92, 65, and 122 are supplied with the backup power supply voltage Vbk via the power supply voltage path VL2, the diode D2, and the common path VL3.

A gimbal board 62 is disposed in the arms 10-1 and 10-2. The gimbal board 62 generates a required voltage from the power supply voltage V0 by a DC/DC converter 63, and supplies the voltage to encoders 120 and 121.

The motor 123, the encoders 64, 120, and 121, and the electromagnetic brakes 65 and 122 described above constitute a driving unit that shifts the orientation and pose of the surgical instrument holding device 16 in each arm 10.

The example of the power supply system illustrated in FIG. 4, FIG. 5, and FIG. 6 described above adopts a configuration in which the power supply voltage V1 of the power supply voltage path VL1 or the backup power supply voltage Vbk of the power supply voltage path VL2 is supplied to the electromagnetic brakes 84, 88, 92, 65, and 122 via the common path VL3, that is, the configuration illustrated in FIG. 3. Specific examples of the electromagnetic brake 100 in FIG. 3 are the electromagnetic brakes 84, 88, 92, 65, and 122.

4. Effects and Modifications of Embodiments

The embodiments described above can provide the following effects.

The surgery assistance device 1 according to some embodiments includes the power supply 32 configured to output the power supply voltage V1 by using the external power supply, the backup power supply 33 configured to output the backup power supply voltage Vbk by using the backup battery 33BT, the power supply voltage path VL1 configured to supply the power supply voltage V1 of the power supply 32 to a plurality of loads, the manual switch 150, and the power supply voltage path VL2 configured to be capable of supplying the backup power supply voltage Vbk of the backup power supply 33 to some of the loads among the plurality of loads when the manual switch 150 is operated.

During a power failure, even when the main power supply is on, the supply of the power supply voltages V0 and V1 by the power supply units 31 and 32 is stopped, and software that performs operation control is also stopped. In such a case, an emergency operation can be realized by supply of the backup power supply voltage Vbk. However, the backup power supply 33 is configured to feed only some of the loads that are supplied with the power supply voltage V1, so that current consumption during the usage of the backup power supply voltage Vbk is reduced. Hence, it suffices for the backup battery 33BT to be of a relatively small size, and the backup battery 33BT is suitable for downsizing the surgery assistance device. An operation for a relatively long time can be performed in a backup state.

In some embodiments, the backup power supply voltage Vbk is supplied to the electromagnetic brake 100 (65, 84, 88, 92, and 122) and the sound module 36 as some of the loads. However, various examples of the loads to be supplied with the backup power supply voltage Vbk are possible. For example, in a case where an actuator for performing an emergency operation at a time of a power failure is included, also assumed is a configuration example in which only the actuator is supplied with the backup power supply voltage Vbk. Of course, there may be adopted a configuration in which only the electromagnetic brake 100 is supplied with the backup power supply voltage Vbk.

In the surgery assistance device 1 according to some embodiments, one or a plurality of electromagnetic brakes 100 (65, 84, 88, 92, and 122) are included as the load(s) to be supplied with the backup power supply voltage Vbk via the power supply voltage path VL2. Thus, a safety measure can be taken by use of the backup power supply voltage Vbk even at a time of a power failure.

When a power failure occurs while the surgical instrument 18 is inserted in the body of the patient 200 during surgery, for example, it is extremely important to remove the surgical instrument 18 for the safety of the patient 200. During the power failure, non-operation of control software is expected, and the joints of the arms 10 or the like cannot be moved because braking is applied by the electromagnetic brake 100 of the non-excitation actuated type.

Accordingly, even at the time of the power failure, the medical staff is enabled to move the arms 10 or the like manually by supplying the electromagnetic brake 100 with a power supply voltage and thus forcibly releasing the braking. It is thereby possible to take a necessary safety measure against a sudden power failure.

As illustrated in FIG. 4, FIG. 5, and FIG. 6, the electromagnetic brakes 65, 84, 88, 92, and 122 and the sound module 36 are fed with the backup power supply voltage Vbk. Limiting feeding targets to a very small number of parts including the electromagnetic brakes results in much lower power consumption than driving the whole of the surgery assistance device, and is hence very effective for downsizing of the mounted backup battery 33BT and long time driving.

The sound module 36 is a part that needs to operate at the time of the power failure in that the sound module 36 performs guide sound output in an emergency.

In other words, feeding the backup power supply voltage Vbk to a small number of loads including the electromagnetic brake (only parts that need to be fed for safety at the time of the power failure) makes it possible to perform a necessary emergency operation while being suitable for downsizing of the surgery assistance device.

In some embodiments, the load(s) supplied with the backup power supply voltage Vbk via the power supply voltage path VL2 by operation of the manual switch 150 is (are) only one or a plurality of electromagnetic brakes. As is understood from FIG. 4, the sound module 36 is supplied with the backup power supply voltage Vbk irrespective of operation of the manual switch 150.

The feeding of the electromagnetic brake 100 (65, 84, 88, 92, and 122) does not need to be performed constantly at the time of the power failure. In some embodiments, the electromagnetic brake 100 is fed with the backup power supply voltage Vbk only when the manual switch 150 is on. This configuration means that the electromagnetic brake 100 is fed only when the medical staff or the like tries to move the arm 10 (surgical instrument 18). That is, the feeding of the electromagnetic brakes 84, 88, 92, 65, and 122 is not always necessary even at the time of the power failure. Hence, unnecessary power consumption is prevented by the intervention of the manual switch 150.

When the braking of the electromagnetic brake 100 is released by unconditional supply of the backup power supply voltage Vbk to the electromagnetic brake 100 at the time of the power failure, the position and pose of the surgical instrument 18 become unstable, which is not desirable from the viewpoint of safety. Accordingly, only the electromagnetic brake 100 is preferably fed strictly on the basis of an intention of the medical staff (operation of the manual switch 150).

In some embodiments, a plurality of surgical instruments 18 are held by a plurality of arms 10, and the manual switch 150 and the power supply voltage path VL2 that conducts according to operation of the manual switch 150 are provided for each arm 10.

Thus, the medical staff can move the arms 10 and the surgical instruments 18 by operating the manual switch 150 for each arm 10 (10-1, 10-2, and 10S). When one arm 10 is operated, the backup power supply voltage Vbk is not supplied to the electromagnetic brakes 100 of the other arms 10. That is, the electromagnetic brakes 100 are not released and moved in the arms 10 not being operated. Hence, it is possible to prevent a danger posed by instability of the pose and the like of the other arms 10 when the three arms 10 are removed from the patient 200 in order.

In some embodiments, the power supply voltage path VL1 and the power supply voltage path VL2 are connected to the common path VL3 on cathode electrode sides of the diodes D1 and D2, respectively, and the electromagnetic brake 100 is supplied with the power supply voltages by the common path VL3.

A feeding path to a specific load (electromagnetic brake 100) can be formed in a simple and appropriate manner by cathode electrodes of the diodes D1 and D2 being connected to each other and the cathode electrodes being connected to the common path VL3.

It should be understood that the present disclosure is not limited to the above embodiments, but various other changes and modifications may be made therein without departing from the spirit and scope of the appended claims.

The invention claimed is:

1. A surgery assistance device comprising:
a plurality of arms, each arm of the plurality of arms being configured to hold a surgical instrument;
a power supply circuit configured to output a power supply voltage received from an external power supply;
a backup power supply circuit configured to output a power supply voltage received from a battery;
a plurality of loads;
a first power supply voltage path configured to supply the power supply voltage of the power supply circuit to the plurality of loads to control the plurality of arms;
a plurality of manual switches;
a second power supply voltage path configured to supply the power supply voltage of the backup power supply circuit to some of the loads among the plurality of loads to control the plurality of arms in response to a manual switch of the plurality of manual switches being operated;
a first diode along the first power supply voltage path connected between the power supply circuit and the some of the loads; and
a second diode along the second power supply voltage path connected between each manual switch and the some of the loads,
wherein each arm has a corresponding manual switch and at least one electromagnetic brake;
wherein the at least one electromagnetic brake is included as the some of the loads and the some of the loads to be supplied with the power supply voltage of the backup power supply circuit via the second power supply voltage path by an operation of the manual switch is only the at least one electromagnetic brake in the arm of the plurality of arms corresponding to the manual switch of the plurality of manual switches that has been operated; and
wherein the first power supply voltage path and the second power supply voltage path are connected to a common path on cathode electrode sides of the first diode and the second diode, respectively, that leads into the some of the loads, and the some of the loads are supplied with the power supply voltage via the common path.

2. The surgery assistance device according to claim 1, wherein
the second power supply voltage path comprises a plurality of second power supply voltage paths, and each of the plurality of manual switches has a corresponding second power supply voltage path of the plurality of second power supply voltage paths.

3. A surgery assistance device comprising:
a battery;
a plurality of loads;
a plurality of manual switches;
a power supply circuit connected to an external power supply and configured to output a first power supply voltage based on power supplied from the external power supply;
a backup power supply circuit connected to the battery and configured to output a second power supply voltage based on power supplied from the battery;
a first power supply voltage path configured to supply the first power supply voltage to the plurality of loads;
a second power supply voltage path configured to supply the second power supply voltage to a portion of the plurality of loads in response to an operation of a manual switch of the plurality of switches;
a first diode along the first power supply voltage path connected between the power supply circuit and the portion of the plurality of loads;
a second diode along the second power supply voltage path connected between the manual switch and the portion of the plurality of loads; and
a plurality of arms configured to hold a plurality of surgical instruments,
wherein each arm of the plurality of arms is configured to hold a respective surgical instrument of the plurality of surgical instruments,
wherein each arm of the plurality of arms has a corresponding manual switch and at least one electromagnetic brake,
wherein the at least one electromagnetic brake is included as the portion of the plurality of loads and the portion of the plurality of loads to be supplied with the power supply voltage of the backup power supply circuit via the second power supply voltage path by the operation of the manual switch is only the at least one electromagnetic brake in the arm of the plurality of arms corresponding to the manual switch of the plurality of manual switches that has been operated, and
wherein the first power supply voltage path and the second power supply voltage path are connected to a common path on cathode electrode sides of the first diode and the second diode, respectively, that leads into the portion of the plurality of loads, and the portion of the plurality of loads are supplied with the first and second power supply voltages via the common path.

4. The surgery assistance device according to claim 3, wherein the second power supply voltage path comprises a plurality of second power supply voltage paths, and
wherein each arm of the plurality of arms is connected one of the plurality of second power supply voltage paths.

5. A surgery assistance device comprising:
a battery;
a plurality of loads;
a plurality of manual switches connected to a portion of the plurality of loads;

a power supply circuit connected to a mains power supply and to the plurality of loads, the power supply circuit being configured to output a first power supply voltage to the plurality of loads;

a backup power supply circuit connected to the battery and to the manual switch;

a first diode connected between the power supply circuit and the portion of the plurality of loads, and a second diode connected between each manual switch and the portion of the plurality of loads; and a plurality of arms configured to hold a plurality of surgical instruments, each arm of the plurality of arms being configured to hold a respective surgical instrument of the plurality of surgical instruments, wherein the backup power supply circuit is configured to output a second power supply voltage to the portion of the plurality of loads in response to the manual switch being closed, wherein each arm of the plurality of arms has a corresponding manual switch and at least one electromagnetic brake, wherein the portion of the plurality of loads to be supplied with the power supply voltage of the backup power supply circuit via the second power supply voltage path by an operation of the manual switch is only the at least one electromagnetic brake in the arm of the plurality of arms corresponding to the manual switch of the plurality of manual switches that has been operated, and wherein a common path is disposed on cathode electrode sides of the first diode and the second diode and leads into the portion of the plurality of loads, and the portion of the plurality of loads are supplied with the first and second power supply voltages via the common path.

6. The surgery assistance device according to claim 5, wherein the plurality of loads comprises one or more circuits or devices and one or more electromagnetic brakes.

7. The surgery assistance device according to claim 3, wherein the plurality of loads comprises one or more circuits or devices and one or more electromagnetic brakes.

8. The surgery assistance device according to claim 5, wherein the plurality of surgical instruments comprises an endoscope or a forceps.

9. The surgery assistance device according to claim 5, wherein the first power supply voltage is a same voltage as the second power supply voltage.

* * * * *